United States Patent
Sugimoto

(10) Patent No.: US 9,464,110 B2
(45) Date of Patent: Oct. 11, 2016

(54) ACYL DIPEPTIDE DERIVATIVE

(71) Applicant: AJINOMOTO CO., INC., Tokyo (JP)

(72) Inventor: Takanori Sugimoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/628,752

(22) Filed: Feb. 23, 2015

(65) Prior Publication Data

US 2015/0166600 A1 Jun. 18, 2015

Related U.S. Application Data

(63) Continuation of application No. PCT/JP2013/072573, filed on Aug. 23, 2013.

(30) Foreign Application Priority Data

Aug. 24, 2012 (JP) ................................. 2012-185061

(51) Int. Cl.
| | | |
|---|---|---|
| C07K 5/078 | (2006.01) | |
| A61K 8/44 | (2006.01) | |
| A61K 8/64 | (2006.01) | |
| A61Q 19/00 | (2006.01) | |
| A61K 8/49 | (2006.01) | |

(52) U.S. Cl.
CPC ............. *C07K 5/06165* (2013.01); *A61K 8/44* (2013.01); *A61K 8/4913* (2013.01); *A61K 8/64* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,772,587 A * | 9/1988 | Tanaka | .................. | C07D 207/08 514/17.7 |
| 6,017,929 A | 1/2000 | Tanaka et al. | | |
| 6,541,629 B1 * | 4/2003 | Osborne | .......... | A61K 47/48215 544/92 |
| 2010/0055062 A1 * | 3/2010 | Arditty | .................... | A61K 8/06 424/70.7 |

FOREIGN PATENT DOCUMENTS

| | | | |
|---|---|---|---|
| CN | 101538236 A | 9/2009 | |
| EP | 0 201 743 A2 | 11/1986 | |
| JP | 62-72696 A | 4/1987 | |
| JP | 64-68396 A | 3/1989 | |
| JP | 1-131107 A | 5/1989 | |
| JP | 2-88549 A | 3/1990 | |
| JP | 5-4912 A | 1/1993 | |
| JP | 8-325131 A | 12/1996 | |
| JP | 2005-289873 A | 10/2005 | |
| JP | 2011-139667 A | 7/2011 | |
| JP | 2011-173856 A | 9/2011 | |
| WO | WO 95/22326 A1 | 8/1995 | |

OTHER PUBLICATIONS

International Search Report issued Nov. 26, 2013 in PCT/JP2013/072573.
Extended European Search Report issued on Mar. 22, 2016 in Patent Application No. 13831331.7.
K. Tsujii, et al., "Effects of Surface Active Compounds on Thermal Denaturation of DNA", Journal of the American Oil Chemist's Society; vol. 54, No. 12, Dec. 1977, XP009188942, pp. 585-586.
Ingrid Grasseri, et al., "Amphiphilic Proline and Prolylproline Derivatives in the Rhodium(I)-Catalyzed Asymmetric Hydrogenation in Water: Chiral Induction as Indication of the Location of Reactants Within the Micelle", Chirality, vol. 10, No. 8, XP055255899, Jan. 1, 1998, pp. 754-759.
James W. Ryan, et al., "A radioassay for aminoacylproline hydrolase (aminopeptidase P) activity", Biochimica et Biophysica Acta, vol. 1119, No. 2, Feb. 26, 1992, XP023579842, pp. 133-139.
Ch. Pulla Rao, et al., "$^{13}$C-n.m.r. studies of the conformational changes in proline oligomers brought about by lithium and calcium salts", International Journal of Biological Macromolecules, vol. 5, No. 5, XP025450861, Oct. 1, 1983, pp. 289-295.
John Haseltine, et al., "Structure dependence in the solvolysis kinetics of amino acid esters", Tetrahedron Letters, vol. 51, No. 25, Jun. 23, 2010, XP027307428, pp. 3280-3283.
Ettore Benedetti, et al., "Solid-State Geometry and Conformation of Linear, Diastereoisomeric Oligoprolines", Biopolymers, vol. 22, No. 1, XP055255908, Jan. 1, 1983, pp. 305-317.

* cited by examiner

*Primary Examiner* — Lianko Garyu
(74) *Attorney, Agent, or Firm* — Oblon, McClelland, Maier & Neustadt, L.L.P.

(57) ABSTRACT

An acyl dipeptide derivative represented by the formula (1):

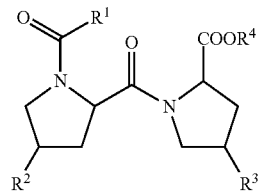

wherein an acyl group represented by $R^1$—CO— is a saturated or unsaturated, straight or branched chain acyl group having 2-24 carbon atoms, $R^2$ and $R^3$ are each independently a hydrogen atom, an OH group or an $OR^5$ group, $R^5$ is a saturated or unsaturated, straight or branched chain hydrocarbon group having 1-6 carbon atoms, and $R^4$ is a hydrogen atom, or a saturated or unsaturated, straight or branched chain hydrocarbon group having 1-6 carbon atoms, or a salt thereof has a superior antimicrobial effect, and a composition containing the compound is superior in the sensory feel.

9 Claims, No Drawings

ACYL DIPEPTIDE DERIVATIVE

CROSS REFERENCES TO RELATED APPLICATIONS

This application is a continuation of International Patent Application No. PCT/JP2013/072573, filed on Aug. 23, 2013, and claims priority to Japanese Patent Application No. 2012-185061, filed on Aug. 24, 2012, all of which are incorporated herein by reference in their entireties.

BACKGROUND OF THE INVENTION

1. Field of the Invention

The present invention relates to a particular acyl dipeptide derivative or a salt thereof, a composition containing the acyl dipeptide derivative or a salt thereof, and a composition containing the acyl dipeptide derivative or a salt thereof (component A) and acyl proline or a salt thereof (component B).

2. Discussion of the Background

In recent years, cosmetic agents using plant-derived starting materials are attracting attention from environmental reasons and in consideration of consumers with preference to natural materials. As the plant-derived starting material, acylamino acid obtained from amino acid and fatty acid is known (patent document 1).

However, cosmetic agents using plant-derived starting materials often show weak antimicrobial property and are not entirely satisfactory in the sensory feel.

DOCUMENT LIST

Patent Document patent document 1: JP-A-5-4912

SUMMARY OF THE INVENTION

The problem of the present invention is to provide a compound having an antimicrobial effect, and a composition superior in the sensory feel, which contains the compound.

Means of Solving the Problems

The present inventors have conducted intensive studies in an attempt to solve the aforementioned problems and found that an acyl dipeptide derivative can be used as a plant-derived starting material and can solve the above-mentioned problems, which resulted in the completion of the present invention.

Accordingly, the present invention includes the following embodiments.

[1] An acyl dipeptide derivative represented by the formula (1):

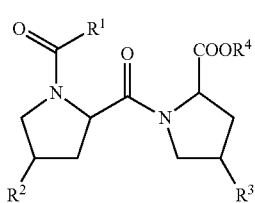

(1)

wherein an acyl group represented by $R^1$—CO— is a saturated or unsaturated, straight or branched chain acyl group having 2-24 carbon atoms, $R^2$ and $R^3$ are each independently a hydrogen atom, an OH group or an $OR^5$ group, $R^5$ is a saturated or unsaturated, straight or branched chain hydrocarbon group having 1-6 carbon atoms, and $R^4$ is a hydrogen atom, or a saturated or unsaturated, straight or branched chain hydrocarbon group having 1-6 carbon atoms, or a salt thereof.

[2] The acyl dipeptide derivative of the above-mentioned [1], wherein, in the formula (1), the acyl group represented by $R^1$—CO— is a saturated or unsaturated, straight or branched chain acyl group having 6-14 carbon atoms, or a salt thereof.

[3] The acyl dipeptide derivative of the above-mentioned [1] or [2], wherein, in the formula (1), the acyl group represented by $R^1$—CO— is a decanoyl group, and $R^2$, $R^3$ and $R^4$ are all hydrogen atoms, or a salt thereof.

[4] A composition comprising the acyl dipeptide derivative of any one of the above-mentioned [1] to [3] or a salt thereof.

[5] A composition comprising
(component A) an acyl dipeptide derivative represented by the formula (1):

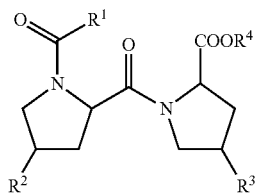

(1)

wherein an acyl group represented by $R^1$—CO— is a saturated or unsaturated, straight or branched chain acyl group having 2-24 carbon atoms, $R^2$ and $R^3$ are each independently a hydrogen atom, an OH group or an $OR^5$ group, $R^5$ is a saturated or unsaturated, straight or branched chain hydrocarbon group having 1-6 carbon atoms, and $R^4$ is a hydrogen atom, or a saturated or unsaturated, straight or branched chain hydrocarbon group having 1-6 carbon atoms, or a salt thereof; and
(component B) acyl proline represented by the formula (2):

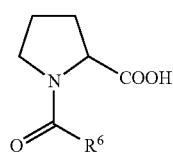

(2)

wherein an acyl group represented by $R^6$—CO— is a saturated or unsaturated, straight or branched chain acyl group having 3-24 carbon atoms,
or a salt thereof.

[6] The composition of the above-mentioned [5], wherein, in the formula (1), the acyl group represented by $R^1$—CO— is a saturated or unsaturated, straight or branched chain acyl group having 6-14 carbon atoms.

[7] The composition of the above-mentioned [5] or [6], wherein, in the formula (1), the acyl group represented by $R^1$—CO— is a decanoyl group, and $R^2$, $R^3$ and $R^4$ are all hydrogen atoms.

[8] The composition of any one of the above-mentioned [4]-[7], wherein the content of the acyl dipeptide derivative or a salt thereof is 0.01 wt %-40 wt %.
[9] The composition of any one of the above-mentioned [5]-[8], wherein the content of the acyl proline or a salt thereof is 0.001 wt %-60 wt %.
[10] The composition of any one of the above-mentioned [5]-[9], wherein the mixing ratio (weight of component A/weight of component B) of the acyl dipeptide derivative or a salt thereof (component A), and acyl proline or a salt thereof (component B) is within the range of 100/1-1/1000.
[11] The composition of any one of the above-mentioned [4]-[10], further comprising polyglycerol ester of fatty acid and/or sucrose ester of fatty acid.
[12] The composition of any one of the above-mentioned [4]-[11], which is a cosmetic agent.

Effect of the Invention

The acyl dipeptide derivative or a salt thereof of the present invention can be used as a plant-derived starting material, and has a superior antimicrobial effect. By using the compound, a composition superior in the antimicrobial property and sensory feel can be provided. Furthermore, by combining the acyl dipeptide derivative, and acyl proline or a salt thereof, a composition further superior in the antimicrobial property and sensory feel can be provided. In the present specification, the antimicrobial property includes antiseptic and/or preservative property.

DETAILED DESCRIPTION OF THE PREFERRED EMBODIMENTS

In the present specification, unless particularly indicated, examples of the "hydrocarbon group" include saturated hydrocarbon groups such as alkyl group, cycloalkyl group and the like, unsaturated hydrocarbon groups such as alkenyl group, alkynyl group, aryl group, aralkyl group and the like, and the like.

In the present specification, unless particularly indicated, examples of the "alkyl group" include straight or branched chain alkyl groups having 1-25 carbon atoms, such as methyl group, ethyl group, propyl group, isopropyl group, butyl group, isobutyl group, sec-butyl group, tert-butyl group, pentyl group, isopentyl group, neopentyl group, 1,2-dimethylpropyl group, 1-ethylpropyl group, hexyl group, isohexyl group, 1,1-dimethylbutyl group, 2,2-dimethylbutyl group, 3,3-dimethylbutyl group, 2-ethylbutyl group, heptyl group, octyl group, nonyl group, decyl group, undecyl group, tridecyl group, tetradecyl group, pentadecyl group, heptadecyl group, octadecyl group, nonadecyl group, icosyl group, eicosyl group, henicosy group, heneicosy group, docosyl group, tricosyl group, tetracosyl group, pentacosyl group, isoheptyl group, isooctyl group, isononyl group, isodecyl group, isoundecyl group, isotridecyl group, isotetradecyl group, isopentadecyl group, isoheptadecyl group, isooctadecyl group, isononadecyl group, isoicosy group, isoeicosy group, isohenicosy group, isoheneicosy group, isodocosyl group, isotricosyl group, isotetracosyl group, isopentacosyl group and the like.

In the present specification, unless particularly indicated, examples of the "cycloalkyl group" include cycloalkyl groups having 3-10 carbon atoms, such as cyclopropyl group, cyclobutyl group, cyclopentyl group, cyclohexyl group, cycloheptyl group, cyclooctyl group and the like, and bridging cycloalkyl groups such as norbornyl and the like.

In the present specification, unless particularly indicated, examples of the "alkenyl group" include straight or branched chain alkenyl groups having 2-25 carbon atoms, such as ethenyl group, propenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, tricosenyl group, tetracosenyl group, pentacosenyl group and the like.

In the present specification, unless particularly indicated, examples of the "alkynyl group" include straight or branched chain alkynyl groups having 2-25 carbon atoms such as ethynyl group, propynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, octadecynyl group, nonadecynyl group, icosynyl group, henicosynyl group, docosynyl group, tricosynyl group, tetracosynyl group, pentacosynyl group and the like.

In the present specification, unless particularly indicated, examples of the "aryl group" include, aryl groups having 6-20 carbon atoms such as phenyl group, naphthyl group, biphenylyl group, anthracenyl group, phenanthrenyl group and the like.

In the present specification, unless particularly indicated, examples of the "aralkyl group" include aralkyl groups having 7-21 carbon atoms such as benzyl group, phenethyl group, phenylpropyl group, naphthylmethyl, benzhydryl, trityl group and the like.

The acyl dipeptide derivative of the present invention (component A) is represented by the formula (1)

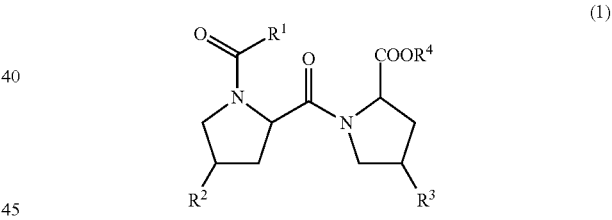

wherein an acyl group represented by $R^1$—CO— is a saturated or unsaturated, straight or branched chain acyl group having 2-24 carbon atoms. Examples thereof include an acetyl group, a propanoyl group (propionyl group), a butanoyl group (butyryl group), an isobutanoyl group (isobutyryl group), a pentanoyl group (valeryl group), an isopentanoyl group (isovaleryl group), a sec-pentanoyl group (2-methylbutyryl group), a tert-pentanoyl group (pivaloyl group), a hexanoyl group, a heptanoyl group, an octanoyl group, a tert-octanoyl group (2,2-dimethylhexanoyl group), a 2-ethylhexanoyl group, a nonanoyl group, an isononanoyl group, a decanoyl group, an isodecanoyl group, an undecanoyl group, a lauroyl group, a myristoyl group, a palmitoyl group, a stearoyl group, a behenoyl group, an undecylenoyl group, an oleoyl group and the like. The long chain acyl group represented by $R^1$—CO— is preferably an acyl group derived from fatty acid having a single composition, but may be an acyl group derived from naturally-obtained mixed fatty acid such as coconut oil fatty acid, castor oil fatty acid, olive oil fatty acid, palm oil fatty acid and the like, or fatty acid (including branched fatty acid) obtained by synthesis. Of these, one kind may be used, and two or more kinds selected from the above-mentioned group may be used as a mixture. The acyl group represented by $R^1$—CO— is preferably a saturated or unsaturated, straight or branched chain acyl group having 4-18 carbon atoms, more preferably a saturated or unsaturated, straight or branched chain acyl group having 6-14 carbon atoms, further preferably a saturated or unsaturated, straight or branched chain acyl group having 10-12 carbon atoms, and further preferably a decanoyl group. An acyl group induced from saturated fatty acid is more preferable than an acyl group induced from unsaturated fatty acid.

That is, $R^1$ is a saturated or unsaturated, straight or branched chain hydrocarbon group having 1-23 carbon atoms. The number of carbon atoms is preferably 3-17, more preferably 5-13, further preferably 9-11, and most preferably 9. The hydrocarbon group is preferably an alkyl group. Specific examples thereof include saturated or unsaturated, straight or branched chain alkyl groups having 1-23 carbon atoms such as methyl group, ethyl group, propyl group, isopropyl group, butyl group, isobutyl group, sec-butyl group, tert-butyl group, pentyl group, isopentyl group, neopentyl group, 1,2-dimethylpropyl group, 1-ethylpropyl group, hexyl group, isohexyl group, 1,1-dimethylbutyl group, 2,2-dimethylbutyl group, 3,3-dimethylbutyl group, 2-ethylbutyl group, heptyl group, octyl group, nonyl group, decyl group, undecyl group, tridecyl group, tetradecyl group, pentadecyl group, heptadecyl group, octadecyl group, nonadecyl group, icosyl group, eicosyl group, henicosyl group, heneicosyl group, docosyl group, tricosyl group, tetracosyl group, pentacosyl group, isoheptyl group, isooctyl group, isononyl group, isodecyl group, isoundecyl group, isotridecyl group, isotetradecyl group, isopentadecyl group, isoheptadecyl group, isooctadecyl group, isononadecyl group, isoicosy group, isoeicosyl group, isohenicosyl group, isoheneicosyl group, isodocosyl group, isotricosyl group and the like.

In the formula, $R^2$ and $R^3$ are each independently a hydrogen atom, an OH group or an $OR^5$ group, wherein $R^5$ is a saturated or unsaturated, straight or branched chain hydrocarbon group having 1-6 carbon atoms. Examples of the saturated or unsaturated, straight or branched chain hydrocarbon group having 1-6 carbon atoms include saturated or unsaturated, straight or branched chain alkyl groups having 1-6 carbon atoms such as methyl group, ethyl group, propyl group, isopropyl group, butyl group, isobutyl group, sec-butyl group, tert-butyl group, pentyl group, isopentyl group, neopentyl group, 1,2-dimethylpropyl group, 1-ethylpropyl group, hexyl group, isohexyl group, 1,1-dimethylbutyl group, 2,2-dimethylbutyl group, 3,3-dimethylbutyl group, 2-ethylbutyl group and the like. From the aspects of sensory feel and antimicrobial property (antiseptic and/or preservative property), $R^2$ and $R^3$ are desirably each independently a hydrogen atom or an OH group, further desirably a hydrogen atom.

In the formula, $R^4$ is a hydrogen atom, or a saturated or unsaturated, straight or branched chain hydrocarbon group having 1-6 carbon atoms. Examples of the saturated or unsaturated, straight or branched chain hydrocarbon group having 1-6 carbon atoms include saturated or unsaturated, straight or branched chain alkyl groups having 1-6 carbon atoms such as methyl group, ethyl group, propyl group, isopropyl group, butyl group, isobutyl group, sec-butyl group, tert-butyl group, pentyl group, isopentyl group, neopentyl group, 1,2-dimethylpropyl group, 1-ethylpropyl group, hexyl group, isohexyl group, 1,1-dimethylbutyl group, 2,2-dimethylbutyl group, 3,3-dimethylbutyl group, 2-ethylbutyl group and the like. From the aspects of sensory feel and antimicrobial property (antiseptic and/or preservative property), $R^4$ is desirably a hydrogen atom or an ethyl group, further desirably a hydrogen atom.

The two proline skeletons constituting the acyl dipeptide derivative represented by the formula (1) may be each independently an L form, a D form or a mixture thereof, and the both are preferably L forms.

Examples of the salt of the acyl dipeptide derivative of the formula (1) include alkali metal salts such as lithium salt, sodium salt, potassium salt and the like; alkaline earth metal salts such as calcium salt, magnesium salt and the like; ammonium salts such as alkanolamine salt (ethanolamine salt, triethanolamine salt etc.) and the like; basic organic salts such as triethylamine salt, lysine salt, arginine salt and the like, and the like. Of these, sodium salt, potassium salt or ammonium salt is preferable, sodium salt or potassium salt is more preferable, and sodium salt is further preferable, from the aspect of sensory feel (e.g., moist feeling).

The production method of the acyl dipeptide derivative of the present invention is not particularly limited, and the derivative can be prepared by, for example, the Schotten-Baumann method including simultaneously adding dropwise fatty acid chloride represented by $R^1$—COCl and a basic aqueous solution of sodium hydroxide and the like to a basic aqueous solution of dipeptide such as prolylproline and the like and sodium hydroxide and the like. In addition, the derivative can also be synthesized by reacting acylamino acid and amino acid ester with a generally-used condensing agent and the like, and hydrolyzing same by a conventional method as necessary.

The first embodiment of the composition of the present invention is characterized in that it contains an acyl dipeptide derivative represented by the formula (1) or a salt thereof.

The acyl dipeptide derivative or a salt thereof of the present invention provides a superior sensory feel (wetness on application, absorbency, moist feeling and the like) and superior antimicrobial property against various bacteria (*Propionibacterium acnes, Escherichia coli, Staphylococcus aureus, Pseudomonas aeruginosa* and the like), various fungi (*Trichophyton mentagrophytes, Candida albicans, Aspergillus niger, Penicillum funiculosum* and the like) and the like, and can be preferable blended with various compositions. The sensory feel can be evaluated by a sensory test.

Examples of the composition of the first embodiment of the present invention include cosmetic agents, pharmaceutical products (including quasi-drugs) and the like. When the acyl dipeptide derivative or a salt thereof of the present invention is obtained from amino acid and a plant-derived fatty acid, it can be used as a plant-derived starting material. The form of the composition of the first embodiment of the present invention is not particularly limited, and can take any form such as liquid, emulsion, paste, gel, solid, powder and the like, with preference given to emulsion.

While the amount of the acyl dipeptide derivative or a salt thereof in the composition of the first embodiment of the present invention varies depending on the co-existing components, it is preferably 0.01 wt %-40 wt % relative to the total weight of the composition. The lower limit value is more preferably 0.05 wt %, further preferably 0.08 wt %, and further preferably 0.1 wt %. From the aspect of the texture of the composition, the upper limit value is more preferably 35 wt %, more preferably 30 wt %, more preferably 20 wt %, more preferably 15 wt %, further preferably 10 wt %, and further more preferably 5 wt %.

The second embodiment of the composition of the present invention is characterized in that it contains an acyl dipeptide derivative represented by the formula (1) or a salt thereof and acyl proline represented by the formula (2) or a salt thereof.

While the composition of the present invention containing an acyl dipeptide derivative or a salt thereof is a composition superior in a sensory feel and antimicrobial property, a composition further superior in the sensory feel and antimicrobial property can be provided by combining same with acyl proline (component B).

The acyl proline (component B) of the present invention is represented by the formula (2)

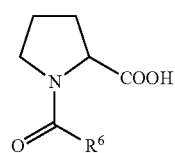

(2)

wherein an acyl group represented by $R^6$—CO— is a saturated or unsaturated, straight or branched chain acyl group having 3-24 carbon atoms. Examples thereof include propanoyl group (propionyl group), butanoyl group (butyryl group), isobutanoyl group (isobutyryl group), pentanoyl group (valeryl group), isopentanoyl group (isovaleryl group), sec-pentanoyl group (2-methylbutyryl group), tert-pentanoyl group (pivaloyl group), hexanoyl group, heptanoyl group, octanoyl group, tert-octanoyl group (2,2-dimethylhexanoyl group), 2-ethylhexanoyl group, nonanoyl group, isononanoyl group, decanoyl group, isodecanoyl group, undecanoyl group, lauroyl group, myristoyl group, palmitoyl group, stearoyl group, behenoyl group, undecylenoyl group, oleoyl group and the like. The long chain acyl group represented by $R^6$—CO— is preferably an acyl group derived from fatty acid having a single composition, but may be an acyl group derived from naturally-obtained mixed fatty acid such as coconut oil fatty acid, castor oil fatty acid, olive oil fatty acid, palm oil fatty acid and the like, or fatty acid (including branched fatty acid) obtained by synthesis. Of these, one kind may be used, and two or more kinds selected from the above-mentioned group may be used as a mixture. The acyl group represented by $R^6$—CO— is preferably a saturated or unsaturated, straight or branched chain acyl group having 4-18 carbon atoms, more preferably a saturated or unsaturated, straight or branched chain acyl group having 6-14 carbon atoms, further preferably a saturated or unsaturated, straight or branched chain acyl group having 10-12 carbon atoms, and further preferably a decanoyl group. An acyl group induced from saturated fatty acid is more preferable than an acyl group induced from unsaturated fatty acid.

That is, $R^6$ is a saturated or unsaturated, straight or branched chain hydrocarbon group having 2-23 carbon atoms. The number of carbon atoms is preferably 3-17, more preferably 5-13, further preferably 9-11, and most preferably 9. The hydrocarbon group is preferably an alkyl group. Specific examples thereof include saturated or unsaturated, straight or branched chain alkyl groups having 2-23 carbon atoms such as ethyl group, propyl group, isopropyl group, butyl group, isobutyl group, sec-butyl group, tert-butyl group, pentyl group, isopentyl group, neopentyl group, 1,2-dimethylpropyl group, 1-ethylpropyl group, hexyl group, isohexyl group, 1,1-dimethylbutyl group, 2,2-dimethylbutyl group, 3,3-dimethylbutyl group, 2-ethylbutyl group, heptyl group, octyl group, nonyl group, decyl group, undecyl group, tridecyl group, tetradecyl group, pentadecyl group, heptadecyl group, octadecyl group, nonadecyl group, icosyl group, eicosyl group, henicosyl group, heneicosyl group, docosyl group, tricosyl group, tetracosyl group, pentacosyl group, isoheptyl group, isooctyl group, isononyl group, isodecyl group, isoundecyl group, isotridecyl group, isotetradecyl group, isopentadecyl group, isoheptadecyl group, isooctadecyl group, isononadecyl group, isoicosy group, isoeicosyl group, isohenicosyl group, isoheneicosyl group, isodocosyl group, isotricosyl group and the like.

Examples of the salt of the acyl proline derivative of the formula (2) include alkali metal salts such as lithium salt, sodium salt, potassium salt and the like; alkaline earth metal salts such as calcium salt, magnesium salt and the like; ammonium salts such as alkanolamine salt (ethanolamine salt, triethanolamine salt etc.) and the like; basic organic salts such as triethylamine salt, lysine salt, arginine salt and the like, and the like. Of these, sodium salt, potassium salt or ammonium salt is preferable, sodium salt or potassium salt is more preferable, and sodium salt is further preferable, from the aspect of moist feeling.

The production method of the acyl proline derivative of the present invention is not particularly limited, and the derivative can be easily produced by combining known methods. To be specific, the derivative can be prepared by the Schotten-Baumann method using proline and acid chloride represented by $R^6$—COCl. In this case, for example, acid chloride and an aqueous solution of a base such as sodium hydroxide and the like are simultaneously added dropwise to a basic aqueous solution of proline and sodium hydroxide and the like. The proline may be an L form, a D form or a mixture thereof, with preference given to an L form.

Since the composition of the second embodiment of the present invention is superior in the sensory feel and antimicrobial property, it can be used as a cosmetic agent or a pharmaceutical product (including quasi-drug), as well as blended with a cosmetic agent or a pharmaceutical product (including quasi-drug). When acyl proline contained in the composition of the second embodiment of the present invention is obtained from amino acid and a plant-derived fatty acid, it can be used as a plant-derived starting material. The form of the composition of the second embodiment of the present invention is not particularly limited, and can take any form such as liquid, emulsion, paste, gel, solid, powder and the like, with preference given to emulsion.

While the amount of the acyl dipeptide derivative or a salt thereof in the composition of the second embodiment of the present invention varies depending on the co-existing components, it is preferably 0.01 wt %-40 wt % relative to the total weight of the composition. The lower limit value is more preferably 0.05 wt %, further preferably 0.08 wt %, and further preferably 0.1 wt %. From the aspect of the texture of the composition, the upper limit value is more preferably 35 wt %, more preferably 30 wt %, more preferably 20 wt %, more preferably 15 wt %, further preferably 10 wt %, and further more preferably 5 wt %.

The amount of acyl proline or a salt thereof in the composition of the second embodiment of the present invention is preferably 0.001 wt %-60 wt % relative to the whole weight of the composition. The lower limit value is more preferably 0.01 wt %, more preferably 0.05 wt %, and preferably 0.1 wt %. From the aspect of the texture of the composition, the upper limit value is more preferably 50 wt %, more preferably 40 wt %, more preferably 30 wt %, more preferably 20 wt %, more preferably 10 wt %, still more preferably 5 wt %.

While the mixing ratio of acyl dipeptide derivative (component A) and acyl proline (component B) in the composition of the second embodiment of the present invention, namely, weight of component A/weight of component B, is not particularly limited, it is preferably within the range of 100/1-1/1000. The upper limit is more preferably not more than 50/1, more preferably not more than 10/1, more preferably not more than 1/1, more preferably not more than 1/10. The lower limit is more preferably not less than 1/500, more preferably not less than 1/250.

In the present invention, polyglycerol ester of fatty acid and/or sucrose ester of fatty acid (component C) can be further added to the composition (including first embodiment and second embodiment, hereinafter the same) to improve the sensory feel.

Examples of the polyglycerol ester of fatty acid include polyglyceryl caprylate, polyglyceryl laurate, polyglyceryl dilaurate, polyglyceryl myristate, polyglyceryl stearate, polyglyceryl distearate, polyglyceryl tristearate, polyglyceryl tetrastearate, polyglyceryl pentastearate, polyglyceryl decastearate, polyglyceryl oleate, polyglyceryl dioleate, polyglyceryl trioleate, polyglyceryl pentaoleate, polyglyceryl decaoleate, polyglyceryl isostearate, polyglyceryl diisostearate and the like.

The amount of polyglycerol ester of fatty acid of the present invention to be blended is preferably 0.001 wt %-60 wt % relative to the whole weight of the composition. The lower limit value is more preferably 0.01 wt %, more preferably 0.05 wt %. From the aspect of the texture of the composition, the upper limit value is more preferably 50 wt %, more preferably 40 wt %, more preferably 30 wt %, more preferably 20 wt %, more preferably 10 wt %, still more preferably 5 wt %.

Examples of the sucrose ester of fatty acid include sucrose laurate, sucrose dilaurate, sucrose myristate, sucrose palmitate, sucrose hexapalmitate, sucrose stearate, sucrose oleate, sucrose distearate, sucrose hexaerucate, sucrose pentaerucate and the like.

The amount of sucrose ester of fatty acid of the present invention to be blended is preferably 0.001 wt %-60 wt % relative to the whole weight of the composition. The lower limit value is more preferably 0.01 wt %, more preferably 0.05 wt %. From the aspect of the texture of the composition, the upper limit value is more preferably 50 wt %, more preferably 40 wt %, more preferably 30 wt %, more preferably 20 wt %, more preferably 10 wt %, still more preferably 5 wt %.

Since the composition of the second embodiment of the present invention is superior in the sensory feel and antimicrobial property, it can be used as a cosmetic agent or a pharmaceutical product (including quasi-drug), as well as blended with a cosmetic agent or a pharmaceutical product (including quasi-drug) together with carrier, excipient and diluent useable in the pertinent technical field. When plant-derived fatty acids are used for polyglycerol ester of fatty acid and sucrose ester of fatty acid, they can be used as plant-derived starting materials.

In the present specification, examples of the cosmetic agent include skin cosmetic agents such as facial cleanser, skin lotion, skin milk, cream, gel, essence, facial pack, facial mask and the like, make-up cosmetic agents such as face powder, foundation, lip rouge, blush, eyeliner, mascara, eye shadow, eyebrow pencil and the like, hair cosmetic agents such as shampoo, rinse, conditioner, hair styling agent, hair treatment and the like.

The cosmetic agent may be blended with components, which can be generally added to cosmetic agents, within the range the effect of the invention is not inhibited. Specific examples thereof include oil, chelating agent, surfactant, powder, amino acids, polyvalent alcohol, polyamino acid and a salt thereof, water-soluble polymer, sugar alcohol and an alkylene oxide adduct thereof, lower alcohol, animals and plants extract, nucleic acid, vitamin, enzyme, anti-inflammatory agent, antimicrobial agent, preservative, antioxidant, UV absorber, adiaphoretic, pigment, coloring agent, oxidation dye, organic and inorganic powder, pH adjuster, pearlizing agent, wetting agent and the like.

Examples of the oil include higher alcohols such as cetyl alcohol, isostearyl alcohol, lauryl alcohol, hexadecyl alcohol, octyldodecanol and the like; fatty acids such as isostearic acid, undecylenoic acid, oleic acid and the like; polyvalent alcohols such as glycerol, sorbitol, ethylene glycol, propylene glycol, polyethylene glycol and the like; esters such as myristyl myristate, hexyl laurate, decyl oleate, isopropyl myristate, hexyldecyl dimethyloctanoate, glycerol monostearate, diethyl phthalate, ethylene glycol monostearate, octyl oxystearate, benzoic acid alkyl ester and the like; hydrocarbons such as liquid paraffin, polyisobutene, petrolatum, squalane and the like; waxes such as lanolin, reduction lanolin, carnauba wax and the like; fats and oils such as mink oil, cacao oil, palm oil, palm kernel oil, camellia oil, sesame oil, castor oil, olive oil and the like; ethylene.α-olefin.cooligomers and the like.

Particularly, examples of the silicone oil include silicone oils selected from cyclic silicones such as ether-modified silicone (methylpolysiloxane, high polymerization methylpolysiloxane, polyoxyethylene.methylpolysiloxane copolymer, polyoxypropylene.methylpolysiloxane copolymer and poly(oxyethylene, oxypropylene).methylpolysiloxane copolymer and the like), stearoxy methylpolysiloxane, stearoxy trimethylsilane, methylhydrogenpolysiloxane, decamethylcyclopentasiloxane, octamethylcyclotetrasiloxane, tetrahydrotetramethylcyclotetrasiloxane, methylcyclopolysiloxane, dodecamethylcyclohexasiloxane and the like; amino-modified silicones such as methylphenylpolysiloxane, trimethylsiloxysilicic acid, aminoethylaminopropylsiloxane.dimethylsiloxane copolymer and the like, silanol-modified polysiloxane, alkoxy-modified polysiloxane, fatty acid-modified polysiloxane, fluorine-modified polysiloxane, epoxy-modified polysiloxane, alkoxy-modified polysiloxane perfluoropolyether, polyvinyl acetate dimethylpolysiloxane, and mixtures thereof.

While the chelating agent is not particularly limited, preferred are, for example, include chelating agent selected from triethylenetetramine, 2-thenoyltrifluoroacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, aurintricarboxylic acid, xylenol orange, 5-sulfosalicylic acid, salicylic acid, pyrocatechol-3,5-disulfonate, 4,5-dihydroxybenzene-1,3-disulfonic acid, 1,2-diaminocyclohexane-N,N,N',N'-tetraacetic acid, citric acid, oxalate, nitrilotriacetic acid, ethylenediamine-N,N,N',N'-tetraacetic acid, acetylacetone and a salt thereof, mixtures thereof and the like.

Examples of the surfactant include anionic surfactants such as N-long chain acyl amino acid salt (N-long chain acyl acidic amino acid salt, N-long chain acyl neutral amino acid salt and the like), N-long chain fatty acid acyl-N-methyltaurine salt, alkylsulfate and an alkylene oxide adduct thereof, fatty acid amide ether sulfate, metal salt and weak base salt of fatty acid, sulfosuccinic acid surfactant, alkylphosphate and an alkylene oxide adduct thereof, alkylether carboxylic acid and the like; cationic surfactants such as ether surfactants (glycerol ether alkylene oxide adduct and the like), ester surfactants (glycerol ester and alkylene oxide adduct and the like), ether ester surfactants (sorbitan ester and an alkylene oxide adduct thereof and the like), ester surfactants (polyoxyalkylene fatty acid ester and the like), nitrogen-containing non-ionic surfactants (alkylglucosides, hydrogenated castor oil dipyroglutamate and an ethylene oxide adduct thereof, fatty acid alkanolamide and the like), aliphatic amine salts (alkylammonium chloride, dialkylammonium chloride and the like), aromatic quaternary ammonium salt (quaternary ammonium salt thereof, benzalkonium salt and the like), fatty acid acyl arginine ester and the like; and amphoteric surfactant such as betaine surfactant (carboxybetaine and the like), aminocarboxylic acid surfactant, imidazoline surfactant and the like and the like.

Examples of the powder include resin powders such as nylon bead, silicone beads and the like, acylamino acid such as nylon powder, metal fatty acid soap, yellow iron oxide, red iron oxide, black iron oxide, chrome oxide, cobalt oxide, carbon black, ultramarine blue, iron blue, zinc oxide, titanium oxide, zirconium oxide, silicon oxide, aluminum oxide, cerium oxide, micatitanium, boron nitride, barium sulfate, calcium carbonate, magnesium carbonate, aluminum silicate, magnesium silicate, silicon carbide, coloring agent, lake, sericite, mica, talc, kaolin, plate barium sulfate, butterfly barium sulfate, titanium oxide fine particle, zinc oxide fine particle, iron oxide fine particle, acyl lysine, acyl glutamic acid, acyl arginine, acyl glycine and the like, and the like. Furthermore, a powder may be applied with a surface treatment such as silicone treatment, fluorine compound treatment, silane coupling agent treatment, silane treatment, organic titanate treatment, acyl lysine treatment, fatty acid treatment, metal soap treatment, oil treatment, amino acid treatment and the like.

Examples of the amino acid include glycine, alanine, serine, threonine, arginine, glutamic acid, aspartic acid, isoleucine, leucine, valine and the like.

Examples of the polyvalent alcohol include glycerol, ethylene glycol, 1,3-butyleneglycol, propylene glycol, isopreneglycol and the like.

Examples of the polyamino acid and a salt thereof include polyglutamic acid, polyaspartic acid and the like.

Examples of the water-soluble polymer include polyethylene glycol, gum arabic, alginates, xanthan gum, hyaluronic acid, hyaluronic acid salt, chitin, chitosan, water-soluble chitin, carboxyvinyl polymer, carboxymethylcellulose, hydroxyethylcellulose, hydroxypropyltrimethylammonium chloride, poly(dimethylmethylenepiperidium chloride), polyvinylpyrrolidone derivative quaternary ammonium, cationized protein, collagen degradation products and a derivative thereof, acylated protein, polyglycerol and the like.

Examples of the sugar alcohol and an alkylene oxide adduct thereof include mannitol and the like.

Examples of the lower alcohol include ethanol, propanol and the like.

EXAMPLES

While the present invention is explained in more detail in the following by referring to Examples, which are not to be construed as limitative.

Synthetic Example 1

Synthesis of Decanoyl Prolylproline

Decanoyl proline (16.31 g) and proline methyl ester hydrochloride (10.00 g) were dissolved in tetrahydrofuran (60 mL), triethylamine (6.10 g), EDCl (1-ethyl-3-(3-dimethylaminopropyl)carbodiimide hydrochloride) (12.72 g) and 1-hydroxybenzotriazole (10.16 g) were added and the mixture was reacted overnight. The reaction mixture was concentrated, ethyl acetate was added, and the mixture was washed with water, 1M hydrochloric acid, saturated aqueous sodium hydrogen carbonate solution and saturated brine. Water was removed by magnesium sulfate. The organic layer was filtered, magnesium sulfate was removed, and the residue was dried under reduced pressure to give decanoyl prolylproline methyl ester (20.14 g). 17.98 g therefrom was dissolved in methanol (100 g), 4M aqueous sodium hydroxide solution (11.81 g) was added and the mixture was reacted overnight. After neutralization with sulfuric acid, the mixture was extracted with ethyl acetate, and water was removed with magnesium sulfate. The organic layer was filtered, magnesium sulfate was removed, and the residue was dried under reduced pressure to give decanoyl prolylproline (16.41 g).

$^1$H-NMR (400 MHz, CD$_3$OD, r.t.): δ 4.68 (1H, dd, J=3.8, 8.4 Hz), 4.48 (1H, dd, J=4.1, 9.1 Hz), 3.84 (1H, m), 3.70-3.50 (3H, m), 2.38 (2H, t, J=7.8 Hz), 2.33-2.22 (2H, m), 2.13-1.98 (6H, m), 1.61 (2H, m), 1.32 (12H, m), 0.92 (3H, t, J=7.0 Hz)

ESI-MS (negative): m/z 365 [M-H]$^-$

Synthetic Example 2

Synthesis of Decanoyl Hydroxyprolylproline

Decanoyl hydroxyproline (13.79 g) and proline methyl ester hydrochloride (8.41 g) were dissolved in tetrahydrofuran (60 mL), triethylamine (5.38 g), 1-hydroxybenztriazole (7.77 g), and EDCl (1-ethyl-3-(3-dimethylaminopropyl)carbodiimide hydrochloride) (9.73 g) were added and the mixture was reacted overnight. The reaction mixture was concentrated, ethyl acetate was added, and the mixture was washed with water, 1M hydrochloric acid, saturated aqueous sodium hydrogen carbonate solution and saturated brine. Water was removed by magnesium sulfate. The organic layer was filtered, magnesium sulfate was removed, and the residue was dried under reduced pressure to give decanoyl hydroxyprolylproline methyl ester (16.56 g).

The obtained decanoyl hydroxyprolylproline methyl ester (1.00 g) was dissolved in a mixture of methanol (5.00 g) and water (1.00 g), 4M aqueous sodium hydroxide solution (0.76 mL) was added, and the mixture was reacted at room temperature for 6 hr. After completion of the reaction, the mixture was extracted with ethyl acetate, washed with saturated brine, dried over anhydrous magnesium sulfate, and the organic layer was filtered to remove magnesium sulfate. The organic layer was concentrated to give 0.85 g of decanoyl hydroxyprolylproline.

$^1$H-NMR (400 MHz, CD$_3$OD, r.t.): δ 4.78 (1H, t, J=7.8 Hz), 4.54-4.47 (2H, m), 3.88 (1H, m), 3.77-3.64 (2H, m), 3.56 (1H, m), 2.38-2.24 (4H, m), 2.12-2.00 (4H, m), 1.62 (2H, m), 1.31 (12H, m), 0.92 (3H, t, J=6.7 Hz)

ESI-MS (negative): m/z 381 [M-H]$^-$

<Antimicrobial Property Evaluation>

The compound of Synthetic Example 1 was subjected to a minimal growth inhibitory concentration (MIC) test against *Propionibacterium acnes* (*P. acnes*) and *Trichophyton mentagrophytes* (*T. mentagrophytes*). The test method is shown below.

(1) Preparation of Test Bacterial Culture

*Propionibacterium acnes*: Anaerobically cultured in a GAM agar medium at 35° C. for 48 hr. A part thereof was transplanted into a GAM bouillon medium, and anaerobically cultured at 35° C. for 24 hr. The culture medium was diluted with GAM bouillon medium to adjust to about $10^6$ cells/mL and used as a test bacterial culture.

*Trichophyton mentagrophytes*: Test bacteria were cultured in a Sabouraud glucose agar medium at 25° C. for 7-14 days, spore and hypha pick were scraped with a platinum loop, suspended in polysorbate 80 0.05% sterile saline and ground in a homogenizer. The solution was filtered through sterile gauze folded in four, and diluted with polysorbate 80 0.05% sterile saline to adjust to about $10^6$ cells/mL and used as a test bacterial culture.

(2) Preparation of Antimicrobial Agent Dilution Solution

A sample was diluted with sterile purified water to prepare a 100000-1000 μg (active ingredient)/mL dilution series.

(3) Preparation of Antimicrobial Agent-Added Agar Medium

The agar medium was dispensed by 9.0 mL into a test tube and, after autoclave sterilization, and incubated in a molten state at 50° C. Thereto was added the diluted solution (1 mL) of the sample prepared in (2). After addition, the mixture was thoroughly blended in a vortex, poured into a petri dish with a diameter of 60 mm and solidified in a flat plate. The agar medium used was GAM agar medium (35° C., 48 hr anaerobic culture) for *Propionibacterium acnes*, Sabouraud glucose agar medium (25° C., 7 days) for *Trichophyton mentagrophytes*.

(4) Inoculation and Culture

The test bacterial culture prepared in (1) was collected by a disposable loop (diameter 1 mm), and cultured at temperature, time described in (3), on an agar medium containing an antimicrobial agent and a line drawn in about 1 cm length.

(5) Determination

The minimum concentration (MIC) of the antimicrobial agent that completely inhibits growth of the test bacteria was determined.

As a result, the minimal growth inhibitory concentration against *Propionibacterium acnes* was 2000-3000 ppm, and that against *Trichophyton mentagrophytes* was 1000-1500 ppm. The acyl dipeptide derivative of the present invention was found to have a superior antimicrobial effect.

<Evaluation of Sensory Feel>

A cream was prepared at the blending amounts shown in Table 1, and subjected to the following evaluation. Cream was prepared by dissolving each of the components of I and II by heating at 85° C., adding II to I by small portions and, after cooling to room temperature, adding III.

[Evaluation 1: Wetness on Application]

The wetness on application of the prepared composition was evaluated by five professional panelists according to the following evaluation criteria.

4 points: very high wetness is felt on application
3 points: wetness is felt on application
2 points: wetness is felt slightly on application
1 point: wetness is not felt much on application
0 point: wetness is not felt at all on application An average of the professional panelists of not less than 3.5 points was marked with ☉, not less than 2.5 points and less than 3.5 points was marked with ○, not less than 1.5 points and less than 2.5 points was marked with Δ, less than 1.5 points was marked with x.

[Evaluation 2: Absorbency]

The absorbency of the prepared composition was evaluated by five professional panelists according to the following evaluation criteria.

4 points: very good absorbency on application
3 points: good absorbency on application
2 points: ordinary absorbency on application
1 point: somewhat bad absorbency on application
0 point: bad absorbency on application An average of the professional panelists of not less than 3.5 points was marked with ☉, not less than 2.5 points and less than 3.5 points was marked with ○, not less than 1.5 points and less than 2.5 points was marked with Δ, less than 1.5 points was marked with x.

[Evaluation 3: Moist Feeling]

The moist feeling of the prepared composition was evaluated by five professional panelists according to the following evaluation criteria.

4 points: very good moist feeling on application
3 points: good moist feeling on application
2 points: ordinary moist feeling on application
1 point: somewhat bad moist feeling on application
0 point: bad moist feeling on application An average of the professional panelists of not less than 3.5 points was marked with ☉, not less than 2.5 points and less than 3.5 points was marked with ○, not less than 1.5 points and less than 2.5 points was marked with Δ, less than 1.5 points was marked with x.

TABLE 1

|   |   |   | Ex. 1 | Ex. 2 | Ex. 3 | Ex. 4 | Com. Ex. 1 | Com. Ex. 2 |
|---|---|---|---|---|---|---|---|---|
| III | A | compound of Synthetic Example 1 | 0.50 |  | 0.50 | 0.50 |  |  |
|  | A | compound of Synthetic Example 2 |  | 0.50 |  |  |  |  |
|  | B | decanoyl proline |  |  |  | 0.50 |  |  |
|  | B | palmitoyl proline |  |  |  |  |  | 0.50 |
|  |  | citric acid | q.s. | q.s. | q.s. | q.s. | q.s. | q.s. |
| II | C | sucrose palmitate | 0.40 | 0.40 | 0.40 |  | 0.40 | 0.10 |
|  | C | polyglyceryl-10 stearate |  |  |  | 0.50 |  |  |
|  |  | xanthan gum | 0.20 | 0.20 | 0.20 | 0.20 | 0.20 | 0.20 |
|  |  | water | balance | balance | balance | balance | balance | balance |
|  |  | sodium stearoyl glutamate | 0.10 | 0.10 | 0.10 | 0.10 | 0.10 | 0.40 |
| I |  | squalane | 5.00 | 5.00 | 5.00 | 5.00 | 5.00 | 5.00 |
|  |  | jojoba oil | 5.00 | 5.00 | 5.00 | 5.00 | 5.00 | 5.00 |

TABLE 1-continued

|  |  | Ex. 1 | Ex. 2 | Ex. 3 | Ex. 4 | Com. Ex. 1 | Com. Ex. 2 |
|---|---|---|---|---|---|---|---|
|  | stearyl alcohol | 3.80 | 3.80 | 3.80 | 3.80 | 3.80 | 3.80 |
|  | glyceryl stearate | 2.90 | 2.90 | 2.90 | 2.90 | 2.90 | 2.90 |
|  | total | 100 | 100 | 100 | 100 | 100 | 100 |
| sensory feel evaluation | wetness on application | ○ | ○ | ○ | ○ | X | X |
|  | absorbency | ○ | ○ | ⊙ | ○ | X | Δ |
|  | moist feeling | ○ | ○ | ⊙ | ○ | X | Δ |

As is clear from Table 1, the formulation (e.g., Example 1) added with the acyl dipeptide derivative (component A) of the present invention was superior in the wetness on application, absorbency and moist feeling as compared to the formulation (Comparative Example 1) without the addition. Also, it was found that the composition (Example 3) using the acyl dipeptide derivative (component A) of the present invention and particular acyl proline (component B) in combination is further superior in the absorbency and moist feeling.

Preparation Example 1

Preparation of Cream

A cream having the following formulation was prepared. The prepared formulation was superior in antimicrobial property and also superior in wetness, absorbency and moist feeling.

TABLE 2

|  | (mass %) |
|---|---|
| compound of Synthetic Example 1 (decanoyl prolylproline) | 0.50 |
| squalane | 5.00 |
| jojoba oil | 5.00 |
| macadamia nut oil | 5.00 |
| capric/caprylic triglyceride | 5.00 |
| di(phytosteryl/octyldodecyl)lauroyl glutamate | 1.00 |
| isostearyl hydroxystearate | 2.00 |
| shea butter | 2.00 |
| stearyl alcohol | 3.80 |
| carnauba wax | 0.10 |
| lyceryl stearate | 2.90 |
| xanthan gum | 0.20 |
| sucrose palmitate | 0.40 |
| sodium stearoyl glutamate | 0.10 |
| citrate buffer | q.s. |
| water | balance |
|  | 100.00 |

Preparation Example 2

Preparation of Skin Lotion

A skin lotion having the following formulation was prepared. The prepared formulation was superior in antimicrobial property and also superior in wetness, absorbency and moist feeling.

TABLE 3

|  | (mass %) |
|---|---|
| compound of Synthetic Example 2 (decanoyl hydroxyprolylproline) | 0.01 |
| decanoyl proline | 0.50 |
| di(phytosteryl/octyldodecyl)lauroyl glutamate | 0.35 |

TABLE 3-continued

|  | (mass %) |
|---|---|
| cetyl caprylate | 0.15 |
| PPG-8-ceteth-20 | 0.50 |
| PPG-6-decyltetradeceth-30 | 0.50 |
| glycerol | 1.25 |
| water | 5.00 |
| DPG | 2.00 |
| BG | 3.00 |
| citrate buffer | q.s. |
| water | balance |
|  | 100.00 |

The details of the materials use are as described below.
(Component B)
decanoyl proline: Synthesized from proline and decanoyl chloride, by Schotten-Baumann method.
Palmitoyl proline: Synthesized from proline and palmitoyl chloride, by Schotten-Baumann method.
(Component C)
sucrose palmitate: surfhope SE COSME C-1615 (manufactured by Mitsubishi Chemical Foods)
polyglyceryl-10 stearate: ester of stearic acid and polyglycerol-10 (with 10 polymerized glycerols on average),
Decaglyn 1-SV (manufactured by Nikko Chemicals)
(Others)
squalane: squalane (manufactured by Maruha Nichiro)
jojoba oil: purified jojoba oil (manufactured by KOEI KOGYO Co., Ltd.)
stearyl alcohol: Kalcol 8688 (manufactured by Kao Corporation) glyceryl stearate: NIKKOL MGS-BV2 (manufactured by Nikko Chemicals)
sodium stearoyl glutamate: "Amisoft" HS-11P (manufactured by Ajinomoto Co., Inc.)
xanthan gum: Keltrol CG-T (manufactured by Sansho)
macadamia nut oil: macadamia nut oil (Nikko Chemicals manufactured by)
capric/caprylic triglyceride: TCG-M (manufactured by Kokyu Alcohol Kogyo Co., Ltd.)
di(phytosteryl/octyldodecyl)lauroyl glutamate: "Eldew" PS-203 (manufactured by Ajinomoto Co., Inc.)
isostearyl hydroxystearate: SCHERCEMOL SHS Ester (manufactured by GSI Creos)
shea butter: shea butter RF (manufactured by Kokyu Alcohol Kogyo Co., Ltd.)
Carnauba wax: purified carnauba wax (manufactured by CERARICA NODA)
PPG-8-ceteth-20: PBC-44 (manufactured by Nikko Chemicals)
PPG-6-decyltetradeceth-30: PEN-4630 (manufactured by Nikko Chemicals)

INDUSTRIAL APPLICABILITY

The acyl dipeptide derivative or a salt thereof of the present invention can be used as a plant-derived starting material, and has a superior antimicrobial effect. By using the compound, a composition superior in the antimicrobial property (including antiseptic and/or preservative property) and sensory feel (e.g., wetness, absorbency, moist feeling) can be provided. Furthermore, by combining the acyl dipeptide derivative, and acyl proline or a salt thereof, a composition further superior in the antimicrobial property and sensory feel can be provided.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An acyl dipeptide compound represented by formula (1):

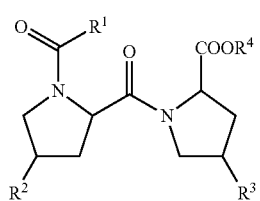

(1)

wherein:
$R^1$—CO— is a decanoyl group; and
$R^2$, $R^3$ and $R^4$ are each a hydrogen atom,
or a salt thereof.

2. A composition, comprising at least one acyl dipeptide compound or a salt thereof according to claim 1.

3. A composition, comprising:
(A) at least one acyl dipeptide compound represented by formula (1):

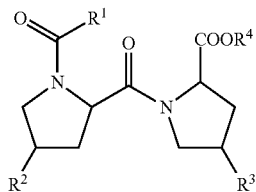

(1)

wherein:
$R^1$—CO— is a decanoyl group; and
$R^2$, $R^3$ and $R^4$ are each a hydrogen atom,
or a salt thereof and
(B) at least one acyl proline represented by formula (2):

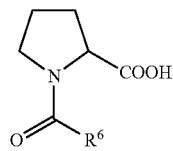

(2)

wherein:
$R^6$—CO— is a saturated or unsaturated, straight or branched chain acyl group having 3 to 24 carbon atoms,
or a salt thereof.

4. A composition according to claim 3, which comprises said at least one acyl dipeptide compound or salt thereof (A) in an amount of 0.01 wt % to 40 wt %, based on the total weight of said composition.

5. A composition according to claim 3, which comprises said at least one acyl proline or salt thereof (B) in an amount of 0.001 wt % to 60 wt %, based on the total weight of said composition.

6. A composition according to claim 3, which comprises said at least one acyl dipeptide compound or salt thereof (A) and said at least one acyl proline or salt thereof (B) in a weight ratio (weight of component A/weight of component B) within the range of 100/1-1/1000.

7. A composition according to claim 3, further comprising at least one polyglycerol ester of fatty acid and/or at least one sucrose ester of fatty acid.

8. A composition according to claim 3, which is in a form of a cosmetic agent.

9. A composition according to claim 7, which is in a form of a cosmetic agent.

* * * * *